(12) United States Patent
Stomp et al.

(10) Patent No.: US 7,709,699 B2
(45) Date of Patent: May 4, 2010

(54) USE OF DUCKWEED IN HIGH THROUGHPUT SCREENING

(75) Inventors: Anne-Marie Stomp, Moncure, NC (US); Lynn Dickey, Cary, NC (US); Billy Houghteling, Raleigh, NC (US); Nirmala Rajbhandari, Apex, NC (US)

(73) Assignee: Biolex Therapeutics, Inc., Pittsboro, NC (US)

( * ) Notice: Subject to any disclaimer, the term of this patent is extended or adjusted under 35 U.S.C. 154(b) by 334 days.

(21) Appl. No.: 10/158,243

(22) Filed: May 30, 2002

(65) Prior Publication Data

US 2003/0033630 A1 Feb. 13, 2003

Related U.S. Application Data

(60) Provisional application No. 60/294,351, filed on May 30, 2001.

(51) Int. Cl.
*A01H 1/00* (2006.01)
*A01H 9/00* (2006.01)
*A01H 11/00* (2006.01)
*C12N 5/04* (2006.01)
*C12N 5/10* (2006.01)
*B01L 3/00* (2006.01)

(52) U.S. Cl. .................. 800/294; 435/419; 435/469; 435/69.4; 435/69.51; 800/295; 800/300; 422/102

(58) Field of Classification Search .............. 435/6, 435/419, 469; 702/19; 800/294, 295, 300; 422/102

See application file for complete search history.

(56) References Cited

U.S. PATENT DOCUMENTS

| | | | | |
|---|---|---|---|---|
| 3,762,909 A | * | 10/1973 | Davie et al. | 71/1 |
| 5,435,098 A | * | 7/1995 | Koide et al. | 47/65 |
| 5,792,931 A | | 8/1998 | Duvick et al. | |
| 6,040,498 A | | 3/2000 | Stomp et al. | |
| 6,096,546 A | | 8/2000 | Raskin | |
| 6,150,158 A | * | 11/2000 | Bhide et al. | 435/286.3 |

FOREIGN PATENT DOCUMENTS

| WO | WO 99/07210 A1 | 2/1999 |
|---|---|---|
| WO | WO 99/19498 A1 | 4/1999 |

OTHER PUBLICATIONS

Birch. Plant Tranformation: Problems and Strategies for Practical Application. Annual Review Plant Physiology. Plant Molecular Biology. 1997, vol. 48, pp. 297-326.*
Chory et al., Current protocol in Molecular Biology. Supplement 47: 2.7.1-2.7.8; 1999.*
Sharp., Dictionary of Chemistry. 2nd ed. England. 1990.*
Negrutiu et al., Plant Molecular Biology. vol. 8; 363-373; 1987.*
Definition for "porous", from Merriam-Webster Online Dictionary. Downloaded from http://www.m-w.com/cgi-bin/dictionary?book=Dictionary&va=porous; downloaded on Jul. 20, 2007.*
Merriam-Webster Online Dictionary. Definition for "frit"; Downloaded on Dec. 18, 2007; Downloaded from http://www.m-w.com/cgi-bin/dictionary?book=Dictionary&va=frit.*
Moon, H.K. and Stomp, A.M., "Effects of Medium Components and Light on Callus Induction, Growth, and Frond Regeneration in *Lemna gibba* (Duckweed)," *In Vitro Cell Dev. Biol.-Plant.*, Jan. 1997, pp. 20-25, vol. 33.
Yamamoto, Y.T., et al., "Genetic Transformation of Duckweed *Lemna gibba* and *Lemna minor*," *In Vitro Cell Dev. Biol.-Plant*, May-Jun. 2001, pp. 349-353, vol. 37.
Weatherwax, S.C., et al., "The Phytochrome Response of the *Lemna gibba NPR1* Gene is Mediated Primarily through Changes in Abscisic Acid Levels," *Plant Physiol.*, 1998, pp. 1299-1305, vol. 116.

* cited by examiner

*Primary Examiner*—Sue Liu
(74) *Attorney, Agent, or Firm*—Alston & Bird LLP

(57) ABSTRACT

Methods for high-throughput screening in duckweed are disclosed. In one aspect, these methods are used to identify nucleotide sequences encoding polypeptides of interest. In another aspect, these methods are used to identify nucleotide sequences that modulate the expression of a target nucleotide sequence. The methods combine the predictive benefits of screening in whole plants with the speed and efficiency of a high throughput system.

15 Claims, No Drawings

USE OF DUCKWEED IN HIGH THROUGHPUT SCREENING

CROSS-REFERENCE TO RELATED APPLICATIONS

This application claims the benefit of U.S. provisional application Ser. No. 60/294,351, filed May 30, 2001, which is hereby incorporated in its entirety by reference herein.

FIELD OF THE INVENTION

The present invention relates to methods for high throughput screening using duckweed.

BACKGROUND OF THE INVENTION

The duckweeds are the sole members of the monocotyledonous family Lemnaceae. The four genera and 34 species are all small, free-floating, fresh-water plants whose geographical range spans the entire globe (Landolt (1986) *Biosystematic Investigation on the Family of Duckweeds: The Family of Lemnaceae—A Monograph Study* Geobatanischen Institut ETH, Stiftung Rubel, Zurich). Although the most morphologically reduced plants known, most duckweed species have all the tissues and organs of much larger plants, including roots, stems, flowers, seeds and fronds. Duckweed species have been studied extensively and a substantial literature exists detailing their ecology, systematics, life-cycle, metabolism, disease and pest susceptibility, their reproductive biology, genetic structure, and cell biology. (Hillman (1961) *Bot. Review* 27: 221; Landolt (1986) *Biosystematic Investigation on the Family of Duckweeds: The Family of Lemnaceae—A Monograph Study* Geobatanischen Institut ETH, Stiftung Rubel, Zurich).

The growth habit of the duckweeds is ideal for microbial culturing methods. The plant rapidly proliferates through vegetative budding of new fronds, in a macroscopic manner analogous to asexual propagation in yeast. This proliferation occurs by vegetative budding from meristematic cells. The meristematic region is small and is found on the ventral surface of the frond. Meristematic cells lie in two pockets, one on each side of the frond midvein. The small midvein region is also the site from which the root originates and the stem arises that connects each frond to its mother frond. The meristematic pocket is protected by a tissue flap. Fronds bud alternately from these pockets. Doubling times vary by species and are as short as 20-24 hours (Landolt (1957) *Ber. Schweiz. Bot. Ges.* 67: 271; Chang et al. (1977) *Bull. Inst. Chem. Acad. Sin.* 24:19; Datko and Mudd (1970) *Plant Physiol.* 65:16; Venkataraman et al. (1970) *Z. Pflanzenphysiol.* 62: 316).

Duckweed plant or duckweed nodule cultures can be efficiently transformed by any one of a number of methods including *Agrobacterium*-mediated gene transfer, ballistic bombardment, or electroporation. Stable duckweed transformants can be isolated by transforming the duckweed cells with both the nucleotide sequence of interest and a gene which confers resistance to a selection agent, followed by culturing the transformed cells in a medium containing the selection agent. See U.S. Pat. No. 6,040,498 and U.S. Provisional Patent Application No. 60/221,705; herein incorporated by reference in their entirety.

Recent advances in plant genome sequencing have provided a wealth of information regarding the sequence of genes encoding novel polypeptides and the associated nucleotide sequences that may serve to regulate the expression of these coding sequences. However, these sequence data provide no information regarding the precise role of these nucleotide sequences in physiologically-important processes.

To determine or confirm the function of novel genes, it is generally necessary to express these genes in vivo. When screening nucleotide sequences to determine their activities in plants, the highest predictive success comes from tests for the activity of the sequence in a whole plant. However, greenhouse testing of intact plants grown in soil is time- and space-consuming. Large amounts of labor are also required to prepare, care for, and score these screens, and these steps are generally not amenable to automation.

A method for screening for nucleotide sequences in a system that combines the predictive success of whole plant screening with the reduced size and cost of high-throughput screening is desirable. Accordingly, the present invention provides methods for conducting high throughput screens in a duckweed system.

SUMMARY OF THE INVENTION

High throughput methods for determining the biological function of nucleic acid molecules, and for identifying nucleic acid molecules of interest in a duckweed system are provided.

The methods of the invention are amenable to automation to allow for rapid and efficient identification and characterization of nucleic acid molecules. The methods may be performed in a high-density format so that multiple samples may be processed simultaneously. In addition, multiple steps of the method may be performed in the same high-density format. For example, in one embodiment, the transformation, selection, and regeneration of the duckweed culture are all capable of being performed in the same high density format plate. The methods provide for the high speed screening of nucleotide sequences such that a nucleic acid molecule of interest may be identified in a shortened time frame following the transformation of the duckweed culture. Finally, the methods provide for a high efficiency of recovery of transformed duckweed lines.

The methods involve transforming a duckweed plant culture, duckweed nodule culture, duckweed suspension culture, or duckweed protoplast cell culture with a nucleotide sequence. The duckweed system is then manipulated to identify a nucleic acid molecule of interest.

In one embodiment the duckweed plant culture, duckweed nodule culture, duckweed suspension culture, or duckweed protoplast cell culture is transformed with a test nucleotide sequence, and the biological function of the test nucleotide sequence is determined to thereby determine if the test nucleotide sequence is a nucleic acid molecule of interest.

In another embodiment, the duckweed plant culture, duckweed nodule culture, duckweed suspension culture, or duckweed protoplast cell culture is transformed with a reporter nucleotide sequence under conditions such that the reporter nucleotide sequence is integrated into the DNA of the duckweed plant culture, duckweed nodule culture, duckweed suspension culture, or duckweed protoplast culture, and the nucleic acid molecule of interest is identified by determining if the reporter nucleotide sequence is integrated into the duckweed DNA such that it is operably linked to a nucleic acid molecule of interest.

DETAILED DESCRIPTION OF THE INVENTION

The present invention is drawn to methods for the high-throughput screening of nucleic acid molecule in a duckweed system to identify and characterize nucleic acid molecules of interest. These methods combine the predictive success of screening in whole plants with the size, labor, time and cost efficiencies of high-throughput screening typically associated with single cell technology.

Definitions

The methods of the invention are high-throughput screening methods. By "high-throughput method" as used herein is intended a method for which at least one of the following is true:

(1) The method is performed in a high-density format, i.e. in a format such that more than one sample may be processed simultaneously. For example, in some embodiments, at least 12 or more, at least 24 or more, at least 48 or more, at least 96 or more, or at least 384 or more samples may be processed in a single plate or other container. The plate or other container may be specially adapted for the growth, maintenance, and automated handling of duckweed cultures by the addition of a porous support system in each well. See, for example, U.S. Provisional Patent Application Ser. No. 60/294,430 filed on May 30, 2001 and U.S. Utility Patent application Ser. No. 60/294,430 entitled "Plate and Method for High Throughput Screening" filed on May 28, 2002.

(2) The method is performed such that multiple steps, for example, the transformation, selection, and regeneration of the duckweed culture, can be performed in the same high density format plate or container. In one embodiment, two or more of the steps selected from the transformation step, selection step, and regeneration step, are performed in the same plate so that transfer of the duckweed culture is not required between steps.

(3) The method is amenable to automation, i.e. one or more steps of the method may be performed using a laboratory robotics station.

(4) The method allows for the high speed screening of nucleotide sequences. For example, in some embodiments of the present invention the transformed duckweed may be assayed to identify a nucleic acid molecule of interest following as few as 4-16 weeks after transformation, such as within 4 weeks or fewer, within 5 weeks or fewer, within 6 weeks or fewer, within 7 weeks or fewer, within 8 weeks or fewer, within 9 weeks or fewer, within 10 weeks or fewer, within 11 weeks or fewer, within 12 weeks or fewer, within 13 weeks or fewer, within 14 weeks or fewer, within 15 weeks or fewer, or within 16 weeks or fewer (5) The method provides a high efficiency for the recovery of transformed duckweed lines such that at least 30% or more, at least 35% or more, at least 40% or more, at least 45% or more, at least 50% or more, at least 55% or more, at least 60% or more, at least 65% or more, at least 70% or more, at least about 75%, at least about 80% or more, at least about 85% or more, at least about 90% or more, or at least about 95% or more of the duckweed cultures transformed in the method give rise to transgenic duckweed lines comprising a test nucleotide sequence or a reporter nucleotide sequence.

The term "duckweed system" or "duckweed culture" as used herein encompasses duckweed plant cultures, duckweed nodule cultures, duckweed suspension cultures, and duckweed protoplast cell cultures.

The term "duckweed plant culture" as used herein refers to a culture comprising mostly fully differentiated duckweed plants.

The term "duckweed nodule culture" as used herein refers to a culture comprising duckweed cells where at least about 50%, 55%, 60%, 65%, 70%, 75%, 80%, 85%, 90%, 95%, or 100% of the cells are differentiated cells. A "differentiated cell," as used herein, is a cell having at least one phenotypic characteristic (e.g., a distinctive cell morphology or the expression of a marker nucleic acid or protein) that distinguishes it from undifferentiated cells or from cells found in other tissue types. In some embodiments, the duckweed nodule culture comprises duckweed micronodules as described elsewhere herein.

The term "duckweed suspension culture" as used herein refers to a culture comprising dispersed duckweed cells, for example dispersed duckweed callus cells. Generally, a duckweed suspension culture will comprise both single cells and unorganized cellular aggregates of varying sizes.

The term "duckweed protoplast cell culture" refers to a culture comprising duckweed cells where at least about 50%, 60%, 70%, 80% or 90% of the duckweed cells lack a cell wall. Methods for making protoplast cells from plant cells are described, for example, in Eriksson (1995) in *Plant Protoplasts*, Fowke et al., eds., CRC Press, herein incorporated by reference.

The term "biological function" as used herein refers to a biological activity or property of a nucleic acid molecule or polypeptide. For example, biological functions for nucleic acid molecules include modulating biological responses, coding for polypeptides, and modulating the expression of target nucleotide sequences. Examples of biological functions for polypeptides include modulating biological responses, conferring structural properties of interest, conferring biochemical activities of interest, and conferring regulatory activities of interest. Particular, non-limiting examples of modulatory and regulatory activities include the ability to bind a substrate of interest, the ability to bind a ligand of interest, the ability to catalyze a reaction of interest, the ability to modulate a response to a plant hormone, the ability to modulate a response to a plant growth regulator, the ability to modulate a response to environmental perturbation, the ability to modulate a response to physiological perturbation, the ability to modulate a response to one or more pathogens, and the ability to modulate a response to one or more toxins.

The term "expression" as used herein refers to the transcription or translation of a nucleotide sequence.

The term "duckweed" refers to members of the family Lemnaceae. This family currently is divided into four genera and 34 species of duckweed as follows: genus Lemna (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus Spirodela (*S. intermedia, S. polyrrhiza, S. punctata*); genus Wolffia (*Wa. angusta, Wa. arrhiza, Wa. australina, Wa. borealis, Wa. brasiliensis, Wa. columbiana, Wa. elongata, Wa. globosa, Wa. microscopica, Wa. neglecta*) and genus Wolfiella (*Wl. caudata, Wl. denticulata, Wl. gladiata, Wl. hyalina, Wl. lingulata, Wl. repunda, Wl. rotunda*, and *Wl. neotropica*). Any other genera or species of Lemnaceae, if they exist, are also aspects of the present invention. *Lemna* species can be classified using the taxonomic scheme described by Landolt (1986) *Biosystematic Investigation on the Family of Duckweeds: The family of Lemnaceae—A Monograph Study* Geobatanischen Institut ETH, Stiftung Rubel, Zurich.

"Operably linked" as used herein in reference to nucleotide sequences refers to multiple nucleotide sequences that are placed in a functional relationship with each other. For example a promoter nucleotide sequence is operably linked to a second nucleotide sequence when it is positioned such that it can drive the transcription of the second nucleotide sequence.

The methods for identifying a nucleic acid molecule of interest comprise the step of transforming a duckweed plant culture, duckweed nodule culture, duckweed suspension culture, or duckweed protoplast cell culture with nucleotide sequence. In some embodiments, the nucleotide sequence is a test nucleotide sequence or a reporter nucleotide sequence. Any method known in the art may be used to transform the duckweed culture. In one embodiment, the stably transformed duckweed is obtained by one of the gene transfer methods disclosed in U.S. Pat. No. 6,040,498 to Stomp et al., or U.S. Patent Application No. 60/221,705; herein incorporated by reference. The methods described in these references include gene transfer by ballistic bombardment with microprojectiles coated with a nucleic acid comprising the nucleotide sequence of interest (also know as biolistic bombardment, microprojectile bombardment, or microparticle bombardment), gene transfer by electroporation, and gene transfer mediated by *Agrobacterium* comprising a vector comprising the nucleotide sequence of interest. The selection and regeneration of transgenic duckweed lines are described in these references, as well as elsewhere herein. In one embodiment, the stably transformed duckweed is obtained via any one of the *Agrobacterium*-mediated methods disclosed in U.S. Pat. No. 6,040,498 to Stomp et al. The *Agrobacterium* used is *Agrobacterium tumefaciens* or *Agrobacterium rhizogenes*. In another embodiment, the duckweed culture is transformed using PEG-mediated transformation. See, for example, Lazerri (1995) *Methods Mol. Biol.* 49:95-106, Mathur et al. (1998) *Methods Mol. Biol.* 82:267-276, and Datta et al. (1999) *Methods Mol. Biol.* 111:335-347; herein incorporated by reference.

In one embodiment, the duckweed plant culture, duckweed nodule culture, duckweed suspension culture, or duckweed protoplast culture is transformed in a high-density format plate or other container, for example a 24-well plate, 48-well plate, or a 96-well plate. The plate may be adapted for the automated handling of the duckweed cultures by the addition of a porous support in each well. See, for example, U.S. Utility patent application Ser. No. 10/157,562, filed May 29, 2002, now U.S. Pat. No. 7,326,385, entitled "Plate and Method for High Throughput Screening," herein incorporated by reference. In other embodiments, the duckweed culture is transformed in a single container and then the duckweed is transferred to a high-density format. The duckweed may be transferred to the high-density format by hand, or the transfer of duckweed plants, nodules, suspension cells, or protoplasts may be automated using methods known in the art.

The present invention provides methods for the preparation of duckweed nodule cultures that may be easily manipulated using automated procedures. The methods comprise breaking up larger duckweed nodules to produce duckweed "micronodule" cultures. "Micronodules" are duckweed nodules that are of a sufficiently small size that they can be aspirated or dispensed using the nozzle of an automated liquid handler. In some embodiments, the automated liquid handler or automated liquid handler pipette tip is modified to increase the size of the barrel and tip opening so that the micronodules can freely move into and out of the pipette tip. Any method for breaking up the duckweed nodules to produce micronodules may be used, including mechanical methods, enzymatic methods, or methods for growing the duckweed under conditions promoting the formation of micronodules. In one embodiment, the micronodule culture is produced by pushing duckweed nodules through one or more layers of meshed sieve. In particular embodiments, 30 mesh sieves are used. The micronodules may then be transferred to a high-density format plate or other container. The concentration of the micronodules may be adjusted such that most wells of the high density format plate or container will have only one transformation event. The micronodules of the invention show an efficiency of frond regeneration similar to that observed for duckweed nodules that have not been broken into smaller pieces.

In some embodiments of the present invention, the duckweed is transformed by a nucleic acid molecule comprising a test nucleotide sequence. In particular embodiments, the test nucleotide sequence is comprised in an expression cassette having a transcriptional initiation region operably linked to the test nucleotide sequence. The transcriptional initiation region, (e.g., a promoter) may be native or homologous or foreign or heterologous to the host, or may be a naturally occurring sequence or a synthetically-created sequence. By foreign, it is intended that the transcriptional initiation region is not found in the wild-type host into which the transcriptional initiation region is introduced.

Any suitable promoter known in the art can be employed according to the present invention (including bacterial, yeast, fungal, insect, mammalian, and plant promoters). For example, plant promoters, including duckweed promoters, may be used. Exemplary promoters include, but are not limited to, the Cauliflower Mosaic Virus 35S promoter, the opine synthetase promoters (e.g., nos, mas, ocs, etc.), the ubiquitin promoter, the actin promoter, the ribulose bisphosphate (RubP) carboxylase small subunit promoter, and the alcohol dehydrogenase promoter. The duckweed RubP carboxylase small subunit promoter is known in the art (Silverthrone et al. (1990) *Plant Mol. Biol.* 15:49). Other promoters from viruses that infect plants, preferably duckweed, are also suitable including, but not limited to, promoters isolated from Dasheen mosaic virus, Chlorella virus (e.g., the Chlorella virus adenine methyltransferase promoter; Mitra et al. (1994) *Plant Mol. Biol.* 26:85), tomato spotted wilt virus, tobacco rattle virus, tobacco necrosis virus, tobacco ring spot virus, tomato ring spot virus, cucumber mosaic virus, peanut stump virus, alfalfa mosaic virus, sugarcane baciliform badnavirus and the like.

Finally, promoters can be chosen to give a desired level of regulation. For example, in some instances, it may be advantageous to use a promoter that confers constitutive expression (e.g, the mannopine synthase promoter from *Agrobacterium tumefaciens*). Alternatively, in other situations, it may be advantageous to use promoters that are activated in response to specific environmental stimuli (e.g., heat shock gene promoters, drought-inducible gene promoters, pathogen-inducible gene promoters, wound-inducible gene promoters, and light/dark-inducible gene promoters) or plant growth regulators (e.g., promoters from genes induced by abscissic acid, auxins, cytokinins, and gibberellic acid). As a further alternative, promoters can be chosen that give tissue-specific expression (e.g., root, leaf, and floral-specific promoters).

The overall strength of a given promoter can be influenced by the combination and spatial organization of cis-acting nucleotide sequences such as upstream activating sequences. For example, activating nucleotide sequences derived from the *Agrobacterium tumefaciens* octopine synthase gene can enhance transcription from the *Agrobacterium tumefaciens* mannopine synthase promoter (see U.S. Pat. No. 5,955,646 to Gelvin et al.). In the present invention, the expression cassette can contain activating nucleotide sequences inserted upstream of the promoter sequence to enhance the expression of the test nucleotide sequence. In one embodiment, the expression cassette includes three upstream activating sequences derived from the *Agrobacterium tumefaciens* octopine synthase gene operably linked to a promoter derived from an *Agrobacterium tumefaciens* mannopine synthase gene (see U.S. Pat. No. 5,955,646, herein incorporated by reference).

The expression cassette may additionally comprise a transcriptional and translational termination region functional in plants. Any suitable termination sequence known in the art may be used in accordance with the present invention. The termination region may be native with the transcriptional initiation region, may be native with the nucleotide sequence of interest, or may be derived from another source. Convenient termination regions are available from the Ti-plasmid of *A. tumefaciens*, such as the octopine synthetase and nopaline synthetase termination regions. See also Guerineau et al. (1991) *Mol. Gen. Genet.* 262:141; Proudfoot (1991) *Cell* 64:671; Sanfacon et al. (1991) *Genes Dev.* 5:141; Mogen et al. (1990) *Plant Cell* 2:1261; Munroe et al. (1990) *Gene* 91:151; Ballas et al. (1989) *Nucleic Acids Res.* 17:7891; and Joshi et al. (1987) *Nucleic Acids Res.* 15:9627. Additional exemplary termination sequences are the pea RubP carboxylase small subunit termination sequence and the Cauliflower Mosaic Virus 35S termination sequence. Other suitable termination sequences will be apparent to those skilled in the art.

The expression cassettes may contain more than one gene or nucleic acid sequence to be transferred and expressed in the transformed plant. Thus, each nucleic acid sequence will be operably linked to 5' and 3' regulatory sequences. Alternatively, multiple expression cassettes may be provided.

Generally, the expression cassette will comprise a selectable marker gene for the selection of transformed cells or tissues. Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See DeBlock et al. (1987) *EMBO J.* 6:2513; DeBlock et al.(1989) *Plant Physiol.* 91:691; Fromm et al. (1990) *BioTechnology* 8:833; Gordon-Kamm et al. (1990) *Plant Cell* 2:603. For example, resistance to glyphosate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

For purposes of the present invention, selectable marker genes include, but are not limited to, genes encoding neomycin phosphotransferase II (Fraley et al. (1986) *CRC Critical Reviews in Plant Science* 4:1); cyanamide hydratase (Maier-Greiner et al. (1991) *Proc. Natl. Acad. Sci. USA* 88:4250); aspartate kinase; dihydrodipicolinate synthase (Perl et al. (1993) *BioTechnology* 11:715); bar gene (Toki et al. (1992) *Plant Physiol.* 100:1503; Meagher et al. (1996) *Crop Sci.* 36:1367); tryptophan decarboxylase (Goddijn et al. (1993) *Plant Mol. Biol.* 22:907); neomycin phosphotransferase (NEO; Southern et al. (1982) *J. Mol. Appl. Gen.* 1:327); hygromycin phosphotransferase (HPT or HYG; Shimizu et al. (1986) *Mol. Cell. Biol.* 6:1074); dihydrofolate reductase (DHFR; Kwok et al. (1986) *Proc. Natl. Acad. Sci. USA* 83:4552); phosphinothricin acetyltransferase (DeBlock et al. (1987) *EMBO J.* 6:2513); 2,2-dichloropropionic acid dehalogenase (Buchanan-Wollatron et al. (1989) *J. Cell. Biochem.* 13D:330); acetohydroxyacid synthase (U.S. Pat. No. 4,761,373 to Anderson et al.; Haughn et al. (1988) *Mol. Gen. Genet.* 221:266); 5-enolpyruvyl-shikimate-phosphate synthase (aroA; Comai et al. (1985) *Nature* 317:741); haloarylnitrilase (WO 87/04181 to Stalker et al.); acetyl-coenzyme A carboxylase (Parker et al. (1990) *Plant Physiol.* 92:1220); dihydropteroate synthase (sulI; Guerineau et al. (1990) *Plant Mol. Biol.* 15:127); and 32 kDa photosystem II polypeptide (psbA; Hirschberg et al. (1983) *Science* 222:1346 (1983).

Also included are genes encoding resistance to: gentamycin (Carrer et al. (1991) *Plant Mol. Biol.* 17:301-303); chloramphenicol (Herrera-Estrella et al. (1983) *EMBO J.* 2:987); methotrexate (Herrera-Estrella et al. (1983) *Nature* 303:209; Meijer et al. (1991) *Plant Mol. Biol.* 16:807); hygromycin (Waldron et al. (1985) *Plant Mol. Biol.* 5:103; Zhijian et al. (1995) *Plant Science* 108:219; Meijer et al. (1991) *Plant Mol. Biol.* 16:807); streptomycin (Jones et al. (1987) *Mol. Gen. Genet.* 210:86); spectinomycin (Bretagne-Sagnard et al. (1996) *Transgenic Res.* 5:131); bleomycin (Hille et al. (1986) *Plant Mol. Biol.* 7:171); sulfonamide (Guerineau et al. (1990) *Plant Mol. Biol.* 15:127); bromoxynil (Stalker et al. (1988) *Science* 242:419); 2,4-D (Streber et al. (1989) *BioTechnology* 7:811); and phosphinothricin (DeBlock et al. (1987) EMBO J. 6:2513).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. See Yarranton (1992) *Curr. Opin. Biotech.* 3:506; Chistopherson et al. (1992) *Proc. Natl. Acad. Sci. USA* 89:6314; Yao et al. (1992) *Cell* 71:63; Reznikoff (1992) *Mol. Microbiol.* 6:2419; Barkley et al. (1980) *The Operon* 177-220; Hu et al. (1987) *Cell* 48:555; Brown et al. (1987) *Cell* 49:603; Figge et al. (1988) *Cell* 52:713; Deuschle et al. (1989) *Proc. Natl. Acad. Sci. USA* 86:5400; Fuerst et al. (1989) *Proc. Natl. Acad. Sci. USA* 86:2549; Deuschle et al. (1990) *Science* 248:480; Labow et al. (1990) *Mol. Cell. Biol.* 10:3343; Zambretti et al (1992) *Proc. Natl. Acad. Sci. USA* 89:3952; Baim et al. (1991) *Proc. Natl. Acad. Sci. USA* 88:5072; Wyborski et al. (1991) *Nuc. Acids Res.* 19:4647; Hillenand-Wissman (1989) *Topics in Mol. And Struc. Biol.* 10:143; Degenkolb et al. (1991) *Antimicrob. Agents Chemother.* 35:1591; Kleinschnidt et al. (1988) *Biochemistry* 27:1094; Gatz et al. (1992) *Plant J.* 2:397; Gossen et al. (1992) *Proc. Natl. Acad. Sci. USA* 89:5547; Oliva et al. (1992) *Antimicrob. Agents Chemother.* 36:913; Hlavka et al. (1985) *Handbook of Experimental Pharmacology* 78; and Gill et al. (1988) *Nature* 334:721. Such disclosures are herein incorporated by reference.

The above list of selectable marker genes is not meant to be limiting. Any selectable marker gene can be used in the present invention.

The expression cassette comprising a test nucleotide sequence is transformed into a duckweed plant culture, duckweed nodule culture, duckweed suspension culture, or a duckweed protoplast cell culture. The transformed duckweed is then regenerated and assayed to determine whether the test nucleotide sequence has the biological function of interest. It is recognized that the duckweed system may be manipulated to determine the biological function of the test nucleotide.

In one embodiment, the biological function of interest is the ability to modulate a biological or physiological response of interest. This biological response can be any response including response to changes in temperature, response to changes in day length, response to changes in water potential, response to changes in light level, response to pathogen exposure (including exposure to fungal pathogens, viruses, viroids, nematodes, insect pests, and bacterial pathogens), response to toxin exposure (e.g. exposure to high levels of salts, metals including heavy metals, herbicides, or other substances that interfere important physiological functions), response to plant hormones, response to plant growth regulators, or a response to any other environmental perturbation.

To identify a nucleic acid molecule of interest (for example a nucleotide sequence encoding a polypeptide that modulates the response of interest), the response of duckweed containing the test nucleotide sequence assayed. In some embodiments, the response of a duckweed containing the test nucleotide sequence is compared with that of duckweed that does not contain the test nucleotide sequence. The response may be assayed by a change in any phenotype including, for example, growth rate. Detectable differences in the response indicate that the test nucleotide sequence is a nucleic acid molecule interest. The nucleic acid molecule of interest (e.g. encoding the polypeptide that modulates the response of interest) may then be readily identified by correlating the transgenic duckweed line having detectable difference in the biological response to the *E. coli* or *Agrobacterium* line that served as the source of the test nucleotide sequence.

Growth rate can be determined by any method known in the art; for example by wet or dry weight, or nitrogen content. The duckweed cultures may be grown under selective or restrictive conditions. The term "selective" or "restrictive" growth conditions as used herein refers to conditions under which the growth rate of untransformed duckweed is reduced in comparison with the growth rate under optimal conditions. Examples of selective growth conditions include restrictive light level, restrictive pH conditions, or the presence of pathogens or toxins that restrict growth.

In some embodiments, the nucleic acid molecule of interest is a nucleotide sequence encoding a polypeptide having a biological function of interest. The biological function of interest can be any biological function, for example, the ability to confer a structural or mechanical property, the ability to bind a particular substrate, the ability to bind a particular ligand, the ability to bind a particular receptor, or the ability to catalyze a particular reaction. In those instances where the polypeptide encoded by the test nucleotide sequence is secreted, the medium of the duckweed culture may be removed to a separate container and assayed for the biological function of interest, for example, a particular structural property, a particular biochemical activity, or the ability to form a complex with a particular ligand, substrate, or other agent. When the polypeptide encoded by the test nucleotide sequence is retained within the duckweed tissue, the tissue is disrupted and the protein is extracted and assayed for the expression of a polypeptide having the biological function of interest. In some embodiments, the disruption, extraction, and/or assay steps are automated.

In some embodiments, the polypeptide having the biological function of interest is a variant of a naturally-occurring polypeptide, and the biological function of interest is a change of at least one property of the polypeptide having the biological function of interest in comparison with the naturally-occurring polypeptide. Methods of making such variants are known in the art and described elsewhere herein. See, Example 2 in the Experimental Section. The property that differs between the polypeptide having the biological function of interest (i.e. the variant) and the naturally-occurring polypeptide may be any property of interest including, but not limited to, a structural property, the ability to bind a substrate, the ability to bind a ligand, the ability to catalyze a reaction of interest, the ability to function under conditions outside biological range, or the ability to modulate a biological response. The polypeptide having the property of interest may be identified as described above.

Each duckweed culture sample may be transformed with a nucleic acid preparation containing sequence variations of only one original nucleotide sequence. Alternatively, each sample may be transformed with a heterogeneous nucleic acid preparation containing a pool of several test nucleotide sequences. Pools of about 3, about 5, about 10, about 15, about 20, about 25, about 30, about 40, about 50, about 60, about 70, about 80, about 90, or about 100 test nucleotide sequence per duckweed culture may be used. In this approach, pools of test nucleotide sequences containing a nucleotide sequence having a biological function of interest are subjected to one or more rounds of subdivision and screening to identify a single nucleic acid molecule of interest. The total number of test nucleotide sequences screened in either approach may be at least 1 or more, at least 10 or more, at least 100 or more, at least 1,000 or more, at least 10,000 or more, at least 100,000 or more, at least 500,000 or more, or at least 1,000,000 or more.

In some embodiments of the present invention, the nucleic acid molecule of interest is identified by transforming duckweed plant culture, duckweed nodule culture, duckweed suspension culture, or duckweed protoplast cell culture with a reporter nucleotide sequence under conditions such that the reporter nucleotide sequence is integrated into the duckweed DNA. The reporter nucleotide sequence comprises a coding sequence for a reporter polypeptide. The reporter polypeptide may be any known in the art including, but not limited to, β-glucuronidase (GUS), luciferase, chloramphenicol acetyltransferase (CAT), or green fluorescent protein (GFP). Methods for the detection of each of these reporter polypeptides are well known in the art.

In some embodiments, the reporter nucleotide sequence lacks a transcriptional initiation nucleotide sequence. In other embodiments, the reporter nucleotide sequence comprises a transcriptional initiation nucleotide sequence. The transcriptional initiation nucleotide sequence may be any known in the art including those described herein. In some embodiments, the transcriptional initiation sequence is a minimal promoter sequence. This allows for the identification of nucleotide sequences serving as transcriptional enhancers when the reporter nucleotide sequence is integrated into the duckweed DNA such that it is operably linked to an enhancer sequence.

The reporter nucleotide sequence may contain a selectable marker as described above to aid in the selection of transgenic plants. Any selectable marker known in the art may be used.

The reporter nucleotide sequence also comprises nucleotide sequences that allow it to integrate into the duckweed DNA. In one embodiment, these nucleotide sequences are transfer DNA (T-DNA) sequences. These sequences are segments of the large Ti (tumor inducing) plasmid harbored by all virulent *Agrobacterium* strains. In one embodiment, the imperfect direct repeat sequences found at the T-DNA sequence borders are inserted at the 5' and 3' ends of the reporter nucleotide sequence. The T-DNA nucleotide sequences of the present invention preferably comprise as least one T-DNA repeat sequence. See, for example WO 93/17116, incorporated herein by reference.

Mobilization of the T-region to the plant cell is mediated by another region of the Ti-plasmid, the vir (virulence) region (reviewed in Zambryski (1988) Annu Rev. Genet. 22:1-30; Zambryski et al. (1989) Cell 56:193-201, and Baron and Zambryski (1996) Curr. Biol. 6:1567-1569). The required vir region may be provided in trans, for example on a second plasmid of a binary plasmid system. See, for example, Hoekema et al. (1983) *Nature* 310:115-120 and Bevan (1984) *Nucl. Acids Res.* 22:8711-8721. In other embodiments, the vector containing the DNA to be transferred is introduced into *Agrobacterium* by triparental mating or electroporation, and homologous recombination takes place between this vector and the acceptor Ti-plasmid.

The claimed methods provide for the identification of various nucleic acid molecules of interest. In one embodiment, the nucleic acid molecule of interest serves as a promoter or enhancer to modulate the transcription of a target nucleotide sequence. Accordingly, the methods may be used to identify promoters and enhancers that are involved in a biological response to a stimulus of interest. Non-limiting examples of stimuli of interest include changes in light, changes in temperature, changes in water potential, changes in day length, changes in plant hormone levels, changes in plant growth regulator levels, exposure to pathogens, and exposure to toxins. To identify a nucleic acid molecule involved in the biological response to the stimulus, the duckweed culture comprising the integrated reporter nucleotide sequence is exposed to the stimulus and the expression of the reporter polypeptide is determined. In those cases where the reporter nucleotide sequence has integrated into the duckweed DNA such that it is operably linked to a promoter or enhancer activated by the stimulus, expression of the reporter polypeptide will be detected. The site of integration of the reporter nucleotide sequence can be identified using portions of the reporter nucleotide sequence as a marker to thereby identify the nucleotide sequence that exerts a modulatory activity in response to the stimulus.

The methods of the invention may be used to identify nucleotide sequences that modulate the transcription of a target nucleotide sequence in a tissue-specific manner. The transgenic duckweed lines are screened to identify those lines expressing the reporter polypeptide only in specific duckweed tissues, for example roots, stems, flowers, seeds, or fronds. The nucleic acid molecule of interest may then be identified as described above.

Nucleic acid molecules that modulate the translation of a target nucleotide sequence (for example the reporter nucleotide sequence) include those that increase transcriptional efficiency, such as leader sequences located in the 5' untranslated region of a target nucleotide sequence (for example, sequences that promote ribosome binding) and those that increase mRNA stability. These nucleotide sequences may be located anywhere within the transcribed portion of a gene, including in the 5' untranslated region of the transcript, in the intronic regions of the gene, and in the 3' untranslated region of the transcript. These sequences are identified when the reporter nucleotide sequence integrates within a transcribed site in a gene. The modulatory translational effects are monitored by assaying for the expression of the reporter polypeptide. As described for transcriptional regulatory sequences described above, nucleotide sequences modulating translation may be regulated by particular stimuli. Accordingly, reporter polypeptide expression in response to a stimulus of interest may be monitored to identify a regulatory nucleotide sequence that is activated in response to the stimulus.

In some embodiments, the reporter nucleotide sequence integrates into the duckweed DNA such that it is operably linked to the coding sequence of a gene whose expression (i.e. transcription and/or translation) is regulated by a stimulus of interest. The nucleotide sequence encoding the reporter polypeptide may be transcribed and translated along with the regulated gene to form a chimeric polypeptide that can be detected using the same techniques used to identify the reporter polypeptide. The expression of the chimeric polypeptide in response to the stimulus of interest can be used to identify transgenic duckweed lines in which the reporter nucleotide sequence is operably linked to a regulated gene that is a nucleic acid molecule of interest. See, Springer (2000) *Plant Cell* 12:1007-1020, herein incorporated by reference.

EXPERIMENTAL

The following examples are offered for purposes of illustration, not by way of limitation.

Example 1

Transformation and Regeneration of Duckweed in a High-Density Format Using Liquid Medium In previously-described experiments, culture of duckweed has been performed on solid media. The purpose of this experiment was to test whether duckweed could be cultured on a porous support saturated with a liquid media. This would make the duckweed transformation, selection, and regeneration steps amenable to automation and demonstrate that the duckweed system is useful for high-throughput screening of nucleotide sequences.

Duckweed nodule cultures (derived from *Lemna minor* strain C016) were transformed with a GUS expression construct using *Agrobacterium*-mediated transformation as follows.

The expression vector used for the GUS expression construct was pBMSP-3. This expression vector is derived from pBMSP-1, which is described in U.S. Pat. No. 5,955,646, herein incorporated by reference. The pBMSP-3 transcriptional cassette contains three copies of a transcriptional activating nucleotide sequence derived from the *Agrobacterium tumefaciens* octopine synthase and, an additional transcriptional activating nucleotide sequence derived from the *Agrobacterium tumefaciens* mannopine synthase gene, a promoter region derived from the *Agrobacterium tumefaciens* mannopine synthase gene, a polylinker site for insertion of the nucleotide sequence encoding the polypeptide of interest, and a termination sequence derived from the *Agrobacterium tumefaciens* nopaline synthase gene. This expression vector also contains a nucleotide sequence coding for neomycin phosphotransferase II as a selectable marker. Transcription of the selectable marker sequence is driven by a promoter derived from the *Agrobacterium tumefaciens* nopaline synthase gene. pBMSP-3 additionally contains a nucleotide sequence corresponding to nucleotides 1222-1775 of the maize alcohol dehydrogenase gene (GenBank Accession Number X04049) inserted between the promoter and the polylinker. To make the GUS expression construct used in this example, a GUS coding sequence and a kanamycin resistance gene were inserted into the pBMSP-3 expression vector.

*Agrobacterium tumefaciens* strain Egs05 transformed with the GUS expression construct was grown on YEB medium (1 g/L yeast extract, 5 g/L beef extract, 5 g/L peptone, 5 g/L sucrose, 0.5 g/L $MgSO_4$) containing streptomycin at 500 mg/L, spectinomycin at 50 mg/L and kanamycin sulfate at 50 mg/L.

Duckweed nodule cultures for transformation were prepared as follows. Duckweed fronds were separated, the roots were cut off with a sterile scalpel, and the fronds are placed, ventral side down, on Murashige and Skoog medium (catalog number M-5519; Sigma Chemical Corporation, St. Louis, Mo.) pH 5.6, supplemented with 5 µM 2,4-dichlorophenoxyacetic acid, 0.5 µM 1-Phenyl-3(1,2,3-thiadiazol-5-yl) urea thidiazuron (Sigma P6186), 3% sucrose, 0.4 Difco Bacto-agar (Fisher Scientific), and 0.15% Gelrite (Sigma). Fronds were grown for 5-6 weeks. At this time, the nodules (small, yellowish cell masses) appeared, generally from the central part of the ventral side. This nodule tissue pieces (average size 3-6 mg) were detached from the mother frond and cultured in Murashige and Skoog medium supplemented with 3% sucrose, 0.4% Difco Bacto-agar, 1 µM 2,4-dichlorophenoxyacetic acid, and 2 µM benzyladenine.

Duckweed nodule cultures were transformed as follows. The appropriate *Agrobacterium tumefaciens* strain was grown on a YEB agar plate with 50 µg/L kanamycin and 100 µM acetosyringone, and the fully grown plate was resuspended in 100 mls of Murashige and Skoog medium supplemented with 0.6 M mannitol and 100 µM acetosyringone. Nodule culture tissue was inoculated by immersing in the solution of resuspended bacteria for 1-2 minutes, blotted to remove excess fluid, and plated on co-cultivation medium consisting of Murashige and Skoog medium supplemented with auxin and cytokinin optimized to promote nodule growth and 100 µM acetosyringone. The nodule cultures were then incubated in darkness for 2 days.

For selection, nodule cultures were transferred to agar plates (Treatment 1, see below) or 24-well plates adapted with polyethylene supports as described in U.S. Provisional Patent Application Ser. No. 60/294,430 filed May 30, 2001 and U.S. Utility Patent Application Ser. No. 10/157,652 entitled, "Plate and Method for High Throughput Screening" filed May 28, 2002 (Treatment 2, see below). To prepare the polyethylene support (frit) the 24-well plate, hydrophilic polyethylene (1/16 of inch thick) was cut into the size to fit into 24-well plate, and a hole was drilled in the middle for media exchange. These frits were autoclaved, dried and put into 24-well plate smooth surface up. The frits were wetted with 560 µl of Murashige and Skoog medium pH 5.6 with 3% sucrose, 1 µM 2,4-dichlorophenoxyacetate, 2 µM benzyladenine and one of the following treatments:

Treatment 1: (agar plates) 200 mg/L kanamycin sulfate and 500 mg/L cefotaxime
Treatment 2: (24-well plate) 200 mg/L kanamycin sulfate and 500 mg/L cefotaxime and cultured for four days under continuous light (20-40 µM/m²·sec). On day 4, the transformed nodule cultures of Treatment 1 were transferred to an agar plate containing 0.5× Schenk and Hildebrandt medium with 3% sucrose, 200 mg/L kanamycin sulfate and 500 mg/L cefotaxime. For the nodule cultures of Treatment 2, the medium was changed to 0.5× Schenk and Hildebrandt medium containing 3% sucrose, 200 mg/L kanamycin and 500 mg/L cefotaxime for 12 wells, and to 0.5× Schenk and Hildebrandt medium containing 200 mg/L kanamycin and 300 mg/L cetylpyridinum chloride for the remaining 12 wells. These nodule cultures were incubated under full light. After 6 days, tissue from several samples was stained to monitor GUS expression. The results were as follows:

| Treatment 1 | |
|---|---|
| Sample Number | Staining Pattern |
| 2 | patchy |
| 5 | large areas of staining |
| 8 | 2 small blue spots |
| 11 | patchy blue |
| 18 | patchy blue |
| 20 | no blue staining |
| 24 | small blue spots |

The nodule cultures were incubated for 7 additional weeks and monitored for the regeneration of duckweed fronds. The results from the Treatment 2 wells grown with cefotaxime are shown below:

| Sample | Weeks to Regeneration | GUS Staining |
|---|---|---|
| 1 | No regenerated fronds | N/D |
| 2 | 10 weeks | N/D |
| 3 | 7 weeks | Positive |
| 4 | No regenerated fronds | N/D |
| 5 | 13 weeks | Positive |
| 6 | 13 weeks | Positive |
| 7 | 9 weeks | Positive |
| 8 | 8 weeks | Positive |
| 9 | 9 weeks | Positive |
| 10 | 13 weeks | Negative |
| 11 | 13 weeks | Negative |
| 12 | No regenerated fronds | N/D |

The transformation efficiency in this experiment was at least 50%. It was observed that duckweed cultures grown on the polyethylene supports produced regenerated fronds more quickly than those grown on agar plates, and gave a higher transformation efficiency. Thus, in addition to demonstrating that duckweed may be cultured in liquid media, this experiment shows that the use of a polyethylene support for culturing the duckweed increased the transformation efficiency and decreased the time required to produced transgenic duckweed lines. These findings demonstrate that the duckweed system provides a valuable approach for whole-plant based screening of nucleotide sequences.

Example 2

Transformation and Regeneration of Duckweed in a High Density Format Using Kanamycin as a Selectable Marker In this example, expression vectors, *Agrobacterium* strains, and duckweed nodule cultures were as described in Example 1. The nodule cultures used in this experiment were 2 weeks old. Co-cultivation was performed as described in Example 1. For decontamination and selection, nodule cultures were transferred to a 24-well plate adapted with polyethylene supports containing Murashige and Skoog medium pH 5.6 with 3% sucrose, 1 µM 2,4-dichlorophenoxyacetate, 2 µM benzyladenine, 500 mg/L cefotaxime and 200 mg/L kanamycin sulfate.

The following day, the medium in the 24-well plates was exchanged as follows. The old medium was removed, and 200 µl of fresh medium was added. Excess medium was removed. 200 µl additional medium was added, and removed as described. 200 µl additional medium was added. If medium rose above level of polyethylene support, excess was removed.

On the next day, the medium in the 24-well plates was exchanged as described above. The medium was then changed every two days for approximately 2 additional weeks. At this point, the growth of the nodule cultures was monitored. 20 of the 24 wells contained live callus cells.

Subsequently, nodule cultures were maintained in 0.5× Schenk and Hildebrandt medium containing 3% sucrose, 200 mg/L kanamycin and 500 mg/L cefotaxime, and medium exchanges were performed every two days for approximately four weeks, and then once a week for four additional weeks. Approximately one week after the shift to Schenk and Hildebrandt medium, cells from 5 wells were stained to detect GUS expression. The results are as follows:

| Sample Number | Staining |
| --- | --- |
| 1 | large and small GUS+ patches |
| 4 | large and small GUS+ patches |
| 8 | large and small GUS+ patches |
| 18 | ~25% of callus is GUS+ |
| 21 | large GUS+ patches |

After 8 weeks under selection, the duckweed cultures exhibited three growth patterns. 16% of the cultures exhibited fast growth, where the well was almost completely filled with duckweed fronds; 62% of the cultures exhibited medium growth, where the well was approximately half filled with duckweed fronds, and 12% of the samples exhibited slow growth, where less than half of the well was filled with duckweed fronds.

After 11 weeks under selection, 18 of the 24 duckweed cultures contained regenerating fronds, giving an overall transformation efficiency of greater than 75%.

Example 3

Transformation and Regeneration of Duckweed in a High Density Format Using G418 as a Selectable Marker The purpose of this experiment was to test methods for further increasing duckweed transformation efficiency and reducing the time required to regenerate transgenic duckweed lines.

In this example, expression vectors and *Agrobacterium* strains were as described in Example 1. Duckweed nodules were derived from *L. minor* strain 8627. The nodule cultures were prepared essentially as described in Example 1, with the exception that some nodule tissue samples were cultured in Murashige and Skoog medium supplemented with 3% sucrose, 0.4% Difco Bacto-agar, 1 µM 2,4-dichlorophenoxyacetic acid, and 2 µM benzyladenine (referred to as "control" samples) and some nodule tissue samples were grown on 0.5× Schenk and Hildebrandt medium containing the same additions (referred to as "pretreated" samples).

Co-cultivation was performed as described in Example 1. For decontamination and selection, nodule cultures were transferred to a 24-well plate adapted with porous polyethylene supports containing 560 µl per well Murashige and Skoog medium pH 5.6 with 3% sucrose, 1 µM 2,4-dichlorophenoxyacetate, 2 µM benzyladenine, 500 mg/L cefotaxime and G418 at a concentration of 25 mg/L, 50 mg/L, 100 mg/L, or 200 mg/L.

The duckweed medium was exchanged as described in Example 2. The G418 provided strong selective pressure, so that untransformed callus was killed after 3 weeks of selection. A large number of regenerated duckweed fronds were observed after only six weeks of selection. After eight weeks, the transformation efficiency was determined as shown below

| Treatment | Number of transgenic lines produced (out of 12) | % transformation |
| --- | --- | --- |
| G418-25 | 8 | 66 |
| G418-50 | 10 | 83 |
| G418-100 (pretreated) | 10 | 83 |
| G418-100 (control) | 9 | 75 |
| G418-200 | 9 | 75 |

This example demonstrates that the methods of the invention can be used to produced transgenic duckweed lines in as few as six weeks, with transformation efficiencies greater than 80%.

Example 4

Identification of Protein Variants Having a Biological function of Interest

The following example is directed to the identification of a variant of a naturally-occurring polypeptide, where the variant is different from the naturally-occurring polypeptide in at least one property.

To produce the variants, the coding sequence of the polypeptide is subjected to saturation mutagenesis to generate a population of nucleotide sequence, each one encoding an amino acid variant of the original encoded polypeptide. Such methods are known in the art and are described, for example, is U.S. Pat. Nos. 6,096,548, 6,117,679, 6,132,970, 6,165,793, and 6,180,406; herein incorporated by reference.

To identify a nucleotide sequence encoding a variant having a property of interest, a population of variant nucleotide sequences is produced as described above, cloned into an *Agrobacterium* binary vector, and transformed into *E. coli*. Approximately 5,000-10,000 colonies are picked from this library, and the corresponding plasmids are transformed into *Agrobacterium* by electroporation. Single *Agrobacterium* colonies are picked for use in the transformation of duckweed using automated colony picking technology known in the art (see, for example, Uber et al. (1991) *Biotechniques* 11 (5): 642-647 and Watson et al. (1992) *Nucleic Acids Res.* 20:4599-4606, herein incorporated by reference).

The single colony *Agrobacterium* preparations are added to wells (one, two, or three wells per *Agrobacterium* colony) of a 24-well plate that is specially adapted for the handling of duckweed cultures by the addition of a filter support in each well (see U.S. Provisional Patent Application Ser. No. 60/294,430 filed May 30, 2001 and U.S. Utility Patent Application Ser. No. 10/157,652 entitled, "Plate and Method for High Throughput Screening" filed May 28, 2002, herein incorporated by reference), and duckweed plants, duckweed nodules, or duckweed suspension cells are added to each well. The co-cultivation, selection, and regeneration steps are conducted in the specially-adapted 24-well plate as described in the previous example. All liquid transfers are performed using automated plate handling and liquid handling procedures.

Following regeneration, the transgenic duckweed plants are assayed for the expression of a variant polypeptide having the property of interest. In some instances, the originally encoded polypeptide contains a sequence directing its secretion. In these cases, the media is removed from the transgenic duckweed and assayed to determine the presence of a variant polypeptide having the property of interest. Such assays are conducted using high throughput screening methods well known in the art.

In those instances where the polypeptide is expressed within the duckweed tissue, automated technology is used to disrupt the duckweed tissue and extract the expressed polypeptide. The extract is then assayed for the presence of the variant polypeptide having the property of interest.

If a well containing duckweed expressing a variant of interest contains multiple transgenic lines, the fronds from this well are separated to single individuals and then assayed to determine which individual line expresses the variant polypeptide having the property of interest.

Example 5

Screening cDNA Expression Libraries in Duckweed

This example is directed to screening cDNA libraries for nucleotide sequences modulating a biological response of interest.

A cDNA expression library is transformed into *Agrobacterium* by electroporation, and *Agrobacterium* cultures are derived from single colonies and maintained in 1534 well plates. The transformed *Agrobacterium* is co-cultivated with duckweed cultures as described in the previous example. Transgenic duckweed plants are regenerated as described and then assayed for their response to changes in environmental perturbation, for example temperature changes, day length, water potential changes, light level changes, pathogen exposure, and toxin exposure. A single collection of transgenic duckweed cell lines may be used to screen for encoded proteins involved in a number of different responses.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A high-throughput method for identifying a nucleic acid molecule of interest, said method comprising the steps of:
    (a) transforming a duckweed plant culture, duckweed nodule culture, duckweed suspension culture, or duckweed protoplast cell culture on a porous frit in a high density format plate or container with a test nucleotide sequence comprising a coding sequence for a polypeptide;
    (b) culturing the duckweed plant culture, duckweed nodule culture, duckweed suspension culture, or duckweed protoplast cell culture on the porous frit in a liquid medium under conditions to select for a transformed duckweed plant culture, duckweed nodule culture, duckweed suspension culture, or duckweed protoplast cell culture, wherein the porous frit allows for exchange of the liquid medium in the high density format plate or container;
    (c) culturing the transformed duckweed plant culture, duckweed nodule culture, duckweed suspension culture, or duckweed protoplast cell culture on the porous frit in a liquid medium under conditions such that the polypeptide encoded by the test nucleotide sequence is expressed, wherein the porous frit allows for exchange of the liquid medium in the high density format plate or container; and
    (d) determining whether the polypeptide encoded by the test nucleotide sequence modulates a biological response of the duckweed plant culture, duckweed nodule culture, duckweed suspension culture, or duckweed protoplast cell culture containing the test nucleotide sequence, wherein a test nucleotide sequence that encodes a polypeptide that modulates a biological response is identified as a nucleic acid molecule of interest, and wherein steps (a) through (c) are performed in the same high density format plate or container;
    wherein said method is carried out using an assembly that comprises said high density format plate or container, wherein said plate or container comprises a body having an upper surface, said body defining:
        a first hole having a first hole upper edge defined by the upper surface of the body and a first hole bottom portion defined within the body and below the upper surface of the body, said first hole being configured to receive the porous frit and the culture and to hold the liquid medium;
        a crescent-shaped ledge protruding into the first hole bottom portion and configured to support the porous frit thereon; and
        a second hole having a second hole upper edge defined by the upper surface of the body and a second hole bottom portion defined within the body and below the upper surface of the body, the second hole bottom portion being connected in fluid communication with the first hole bottom portion such that a pipette device can access the first hole through the second hole upper edge to aspirate the liquid medium through vacuum application and refresh the liquid medium by pumping in fresh medium without removal of the culture and the porous frit from the plate or container.

2. The method of claim 1, wherein said biological response is selected from the group consisting of: response to changes in temperature, response to changes in day length, response to changes in water potential, response to changes in light level, response to exposure to pathogens, response to exposure to toxins, response to plant hormones, and response to plant growth regulators.

3. The method of claim 1, wherein growth rate of a duckweed plant culture, duckweed nodule culture, duckweed suspension culture, or duckweed protoplast cell culture that is transformed with the nucleic acid molecule of interest is changed in comparison with the growth rate of a duckweed plant culture, duckweed nodule culture, duckweed suspension culture, or duckweed protoplast cell culture that is not transformed with the nucleic acid molecule of interest, and wherein an ability of the polypeptide to modulate the biological response is determined by determining the growth rate of the duckweed plant culture, duckweed nodule culture, duckweed suspension culture, or duckweed protoplast cell culture transformed with said test nucleotide sequence.

4. The method of claim 3, wherein the growth rate of the duckweed plant culture, duckweed nodule culture, duckweed suspension culture, or duckweed protoplast cell culture transformed with the nucleic acid molecule of interest is increased under selective growth conditions in comparison with the growth rate of the duckweed plant culture, duckweed nodule culture, duckweed suspension culture, or duckweed protoplast cell culture that is not transformed with the nucleic acid molecule of interest under the same selective growth conditions, and the growth rate of the duckweed plant culture, duckweed nodule culture, duckweed suspension culture, or duckweed protoplast cell culture transformed with the test nucleotide sequence is determined under selective growth conditions.

5. The method of claim 3, wherein the growth rate of the duckweed plant culture, duckweed nodule culture, duckweed suspension culture, or duckweed protoplast cell culture transformed with the nucleic acid molecule of interest is decreased under selective growth conditions in comparison with the growth rate of the duckweed plant culture, duckweed nodule culture, duckweed suspension culture, or duckweed protoplast cell culture that is not transformed with the nucleic acid molecule of interest under the same selective growth conditions, and the growth rate of the duckweed plant culture, duckweed nodule culture, duckweed suspension culture, or duckweed protoplast cell culture transformed with the test nucleotide sequence is determined under selective growth conditions.

6. The method of claim 1, wherein the duckweed plant culture, duckweed nodule culture, duckweed suspension culture, or duckweed protoplast cell culture is transformed by inoculation with *Agrobacterium* comprising said test nucleotide sequence.

7. The method of claim 1, wherein the duckweed plant culture, duckweed nodule culture, duckweed suspension culture, or duckweed protoplast cell culture is transformed by ballistic bombardment.

8. The method of claim 1, wherein the duckweed plant culture, duckweed nodule culture, duckweed suspension culture, or duckweed protoplast cell culture is transformed by electroporation.

9. The method of claim 1, wherein a duckweed protoplast cell culture is transformed and the method of transformation is PEG (polyethylene glycol)-mediated transformation.

10. The method of claim 1, wherein the duckweed plant culture, duckweed nodule culture, duckweed suspension culture, or duckweed protoplast cell culture is selected from the group consisting of the genus *Spirodela*, genus *Wolffia*, genus *Wolfiella*, and genus *Lemna*.

11. The method of claim 10 wherein said duckweed plant or duckweed nodule is selected from the group consisting of *Lemna minor, Lemna miniscula, Lemna aequinacitalis*, and *Lemna gibba*.

12. The method of claim 1, wherein an ability of the polypeptide to modulate the biological response is determined by a biochemical assay.

13. The method of claim 1, wherein an ability of the polypeptide to modulate the biological response is determined by a physiological assay.

14. The method of claim 1, wherein an ability of the polypeptide to modulate the biological response is determined by a phenotypic change.

15. The method of claim 1, wherein the polypeptide that modulates the biological response has a binding site for an agent, and presence of said polypeptide that modulates the biological response of interest is determined by detecting formation of a complex between said polypeptide that modulates the biological response and said agent.

* * * * *

UNITED STATES PATENT AND TRADEMARK OFFICE
CERTIFICATE OF CORRECTION

PATENT NO. : 7,709,699 B2  Page 1 of 1
APPLICATION NO. : 10/158243
DATED : May 4, 2010
INVENTOR(S) : Stomp et al.

It is certified that error appears in the above-identified patent and that said Letters Patent is hereby corrected as shown below:

Column 20, line 15:

"aequinacitalis" to --aequinoctialis--

Signed and Sealed this
Fourteenth Day of June, 2011

David J. Kappos
*Director of the United States Patent and Trademark Office*